United States Patent
Kral et al.

(10) Patent No.: US 9,366,639 B2
(45) Date of Patent: Jun. 14, 2016

(54) METHOD AND DEVICE FOR VISUALLY INSPECTING OBJECTS TO BE TESTED DURING THE PRODUCTION AND/OR PACKAGING OF CIGARETTES

(75) Inventors: Vincent Kral, Bremen (DE); Michael Czarnotta, Bremen (DE)

(73) Assignee: Focke & Co. (GmbH & Co. KG), Verden (DE)

( * ) Notice: Subject to any disclaimer, the term of this patent is extended or adjusted under 35 U.S.C. 154(b) by 84 days.

(21) Appl. No.: 14/236,307

(22) PCT Filed: Jul. 13, 2012

(86) PCT No.: PCT/EP2012/002951
§ 371 (c)(1),
(2), (4) Date: Apr. 12, 2014

(87) PCT Pub. No.: WO2013/017198
PCT Pub. Date: Feb. 7, 2013

(65) Prior Publication Data
US 2014/0226892 A1   Aug. 14, 2014

(30) Foreign Application Priority Data

Aug. 2, 2011   (DE) .................. 10 2011 109 143
Sep. 17, 2011   (DE) .................. 10 2011 113 704

(51) Int. Cl.
*G06K 9/00* (2006.01)
*G01N 21/95* (2006.01)
(Continued)

(52) U.S. Cl.
CPC ............ *G01N 21/95* (2013.01); *B65B 19/30* (2013.01); *B65B 57/00* (2013.01);
(Continued)

(58) Field of Classification Search
CPC ........ B65B 19/28; B65B 57/00; B65B 19/22; B65B 19/02; Y10S 131/906; Y10S 209/936; A24C 5/34; G01N 2021/8835; G01N 21/952; G01N 2035/0436; G01N 2033/0081; G06T 2207/10152; G06T 2207/30108; G06T 7/0004; G07C 3/146; G05B 2219/45048; Y10T 436/113332; G01M 3/3272; G01M 3/34

USPC ............ 382/1, 6, 8, 30, 34, 48, 143; 250/221, 250/223; 209/536
See application file for complete search history.

(56) References Cited

U.S. PATENT DOCUMENTS 2,991,879 A * 7/1961 Innocenti ................ B65B 57/02
209/3.1
4,053,056 A * 10/1977 Day ...................... B07C 5/3404
209/536

(Continued)

FOREIGN PATENT DOCUMENTS

DE    4218971 A1    6/1992
DE    10065321 A1    11/2002
(Continued)

OTHER PUBLICATIONS

Deutshces Patent- Und Markenamt, Recherchebericht (Search on related German Patent Application No. 102011113704.5) (Nov. 14, 2011).

(Continued)

*Primary Examiner* — Vu Le
*Assistant Examiner* — Aklilu Woldemariam
(74) *Attorney, Agent, or Firm* — Laurence P. Colton; Smith Tempel Blaha LLC (57) ABSTRACT

A method and a device for the optical testing of objects during the production and/or packaging of cigarettes, in particular of cigarette packs and/or blanks for cigarette packs and/or overprints and/or print substrates on or for cigarette packs, with the aid of a suitable testing device. For at least one feature characterizing the test object, in particular in a visual respect, a set of feature-value alternatives for the corresponding feature that are stored in a memory is displayed on a display means. By means of an input device, one of the displayed feature values of the set of feature-value alternatives is selected. The testing device is automatically set up or preset for the subsequent testing operations, in particular an evaluating device and/or an illuminating device and/or a suitable light detector of the testing device, the selection of the feature value influencing the setting up of the testing device.

20 Claims, 5 Drawing Sheets

(51) Int. Cl.
  *G07C 3/14*   (2006.01)
  *G01N 21/88*  (2006.01)
  *B65B 19/30*  (2006.01)
  *B65B 57/00*  (2006.01)
  *G06T 7/00*   (2006.01)
  *G01N 21/93*  (2006.01)
  *G01N 21/84*  (2006.01)

(52) U.S. Cl.
  CPC ......... *G01N 21/8806* (2013.01); *G06T 7/0004* (2013.01); *G07C 3/143* (2013.01); *G07C 3/146* (2013.01); *G01N 21/93* (2013.01); *G01N 2021/845* (2013.01); *G01N 2021/8835* (2013.01); *G06K 9/00* (2013.01); *G06T 2207/10152* (2013.01); *G06T 2207/30108* (2013.01)

(56) References Cited

U.S. PATENT DOCUMENTS

| | | | | |
|---|---|---|---|---|
| 4,539,836 A * | 9/1985 | Hester | G01M 3/3272 | 73/45.4 |
| 4,643,027 A * | 2/1987 | Deutsch | B65B 43/50 | 53/53 |
| 4,907,607 A * | 3/1990 | Focke | A24C 5/3412 | 131/280 |
| 4,930,344 A * | 6/1990 | Fleenor | G01M 3/3272 | 73/49.3 |
| 4,972,494 A * | 11/1990 | White | B65B 19/28 | 209/535 |
| 5,353,356 A | 10/1994 | Waugh | | |
| 5,383,322 A * | 1/1995 | Collins, Jr. | B65B 19/28 | 209/535 |
| 5,392,359 A | 2/1995 | Futamura | | |
| 5,898,104 A * | 4/1999 | Rohrssen | G01M 3/3272 | 209/540 |
| 6,006,438 A * | 12/1999 | Shrider | B65B 19/28 | 33/613 |
| 6,205,237 B1 * | 3/2001 | Focke | B07C 5/10 | 382/141 |
| 2002/0069705 A1 * | 6/2002 | Stiller | B65B 19/28 | 73/788 |
| 2006/0267536 A1 * | 11/2006 | Linke | B65B 19/02 | 318/625 |
| 2013/0113917 A1 * | 5/2013 | Sato | A24C 5/3412 | 348/86 |
| 2013/0287285 A1 * | 10/2013 | Sato | A24C 5/3412 | 382/141 |

FOREIGN PATENT DOCUMENTS

| | | |
|---|---|---|
| DE | 60100782 T2 | 7/2004 |
| DE | 102006014345 B3 | 8/2007 |
| DE | 102008020239 A1 | 11/2009 |
| EP | 1588945 A1 | 10/2005 |
| JP | 3081603 A | 4/1991 |

OTHER PUBLICATIONS

State Intellectual Property Office of the People's Republic of China, Notification of the First Office Action (on a related application), Sep. 18, 2015.

* cited by examiner

METHOD AND DEVICE FOR VISUALLY INSPECTING OBJECTS TO BE TESTED DURING THE PRODUCTION AND/OR PACKAGING OF CIGARETTES

STATEMENT OF RELATED APPLICATIONS

This patent application claims the benefit of International Patent Application No. PCT/EP2012/002951 having an Internatinoal Filing Date of 13 Jul. 2012, which claims the benefit of German Patent Application No. 10 2011 109 143.6 having a filing date of 2 Aug. 2011 and German Patent Application No. 10 2011 113 704.5 having a filing date of 17 Sep. 2011.

BACKGROUND OF THE INVENTION

1. Technical Field

The invention relates to a method for the optical testing of objects to be tested—test objects—during production and/or packaging of cigarettes, in particular of cigarette packs and/or blanks for cigarette packs and/or overprints and/or print substrates on or for cigarette packs, with the aid of a suitable testing device. The invention also relates to a device for carrying out such a method.

2. Prior Art

Cigarette packs are tested during the production process with suitable testing devices. Such testing devices generally comprise cameras, which record images of the packs and detect packaging defects by means of suitable methods. The production of cigarettes increasingly requires rapid, efficient adaptation to different products. For example, for the production of different products or brands it is required to produce different cigarette packagings on one the same cigarette packaging machine. In this case, the individual units of the packaging machine must be laboriously adapted to the new pack to be produced. The same applies similarly to the aforementioned testing devices.

It is known from the prior art to store for individual product types or brands machine parameters of the packaging machine, which are retrievable in the case of a change of product. In principle, it is conceivable also to store such feature values specifically for testing devices. In other words, when there is a change of brand, feature values stored for the new brand would be reverted to for the testing device. However, this procedure would already be no longer applicable if a certain brand were to be produced for the first time on a packaging machine. In such a case it is not possible at this stage to revert to feature values stored for the brand. In such a case the testing device would once again have to be laboriously set up "manually". This requires considerable know-how and extensive experience of the person performing the setup.

BRIEF SUMMARY OF THE INVENTION

On this basis, it is the object of the present invention to develop further the method and the device of the type mentioned at the beginning, in particular with regard to simplified setting up of the testing device in cases of changes of product.

This object is achieved by a method for the optical testing of objects to be tested—test objects—during the production and/or packaging of cigarettes, in particular of cigarette packs and/or blanks for cigarette packs and/or overprints and/or print substrates on or for cigarette packs, with the aid of a suitable testing device, characterized by the following features: a) for at least one feature characterizing the test object, in particular in a visual respect, a set of feature-value alternatives for the corresponding feature that are stored in a memory is displayed on a display means, for instance a screen; b) by means of an input device, for instance a keyboard or a pointing device, one of the displayed feature values of the set of feature-value alternatives is selected; c) the testing device is automatically set up or preset for the subsequent testing operations, in particular an evaluating device and/or an illuminating device and/or a suitable light detector of the testing device, the selection of the feature value influencing the setting up of the testing device; and d) the test objects are tested with the set-up testing device, and by a device for the optical testing of objects to be tested—test objects—during the production and/or packaging of cigarettes, in particular of cigarette packs and/or blanks for cigarette packs and/or overprints and/or print substrates on or for cigarette packs, in particular for carrying out the above method, with the following features: a) a display device on which, for at least one feature characterizing the test object, in particular in a visual respect, a set of feature-value alternatives for the corresponding feature that are stored in a data memory can be displayed; b) an input device with which a feature value of the displayed set of feature-value alternatives can be selected; c) a control device with which the testing device can be automatically set up, in particular an evaluating device of the testing device, an illuminating device of the testing device and/or a suitable light detector of the testing device, the selection of the feature value influencing the setting up of the testing device.

It is accordingly provided that, in the setting-up operation of the testing device—generally before the beginning of production of the test objects to be tested—, the control of the testing device ensures that, for at least one feature characterizing the test object, in particular in a visual respect, a set of feature-value alternatives for the corresponding feature that are stored in a data memory is displayed to a user on a display means, for instance a screen.

By means of an input device, for instance a keyboard or a pointing device, the user then selects one of the displayed feature values of the set of feature-value alternatives.

The control then automatically sets up or sets the testing device, the selection of the feature value by the operator influencing this setting up. Ultimately, the setting up of the testing device is directly or indirectly dependent on the selected feature-value alternative.

According to the invention, the control generally displays to the user not just one feature with corresponding feature-value alternatives, but multiple features characterizing the test object, for which a separate set of feature-value alternatives is then respectively displayed. In this case, the setting up would not only be dependent on the selected feature value of a feature, but on the or all of the selected feature values of the multiple features.

As far as the setting up of the testing device by the control is concerned, particularly an evaluating device of the testing device and/or an illuminating device of the testing device and/or a suitable light detector of the testing device, such as for instance an optoelectronic testing element, generally an electronic camera, may be correspondingly set up.

Later, the test objects, which are usually being produced for the first time, are then tested in a way known per se by the testing device set up in this way. The testing of the test objects is generally performed—though not necessarily—during the production process of the testing objects.

For example, the testing device may test cigarette packs, for instance banderoles lying on the cigarette pack, while the cigarette packs are being produced by a suitable packaging machine.

The features characterizing the test object, which are displayed to the user and the respective feature values of which the user must determine on the basis of a respective list of feature-value alternatives, generally comprise features that have an influence on the subsequent setting up of the testing device or are important for the setting up of the testing device.

They are preferably features that can be recorded optically by the light detector of the testing device and generally can be analyzed by the evaluating device of the testing device with a suitable image evaluating method.

For example, in the case of optical testing of a cigarette pack being produced for the first time, it may be important to adapt the testing device to the banderole respectively arranged on the cigarette pack to be tested. Directly or indirectly dependent on the arranged banderole, the control may for example set the sensitivity of a camera of the testing device that is directed at the banderole or the illuminating intensity of an illuminating device illuminating the banderole or other operating parameters of the testing device.

The control can in this case display selectably to a user setting up the testing device for example as feature-value alternatives a set of various combinations of top sides of cigarette packs with banderoles arranged on them. Another example would be that the control displays selectably as a set of feature-value alternatives a set of various combinations of bottom sides with bottom folding, the bottom sides and/or the bottom folding of the individual alternatives differing.

In this respect, the banderoles and/or the pack top sides or the bottom sides and/or the bottom foldings of the individual alternatives differ in particular in form or shape, in particular in their peripheral edge contours, and/or in their color and/or in their position or in other visual features.

The displayed feature values of the respective set of feature-value alternatives in this case respectively comprise at least one feature value which corresponds to the feature value that the respective test object to be newly tested has, or which is particularly similar to this value. This can then be selected by the user.

In a particularly preferred embodiment of the invention, the control of the testing device automatically selects in accordance with the feature value selected by the user at least one test method suitable for the test object to be tested from a (maximum) number of test methods that are stored in a data memory and with which test objects can be tested with the testing device. Insofar as feature values for multiple different features were selected by the user—as described further above—this selection is performed by the control in accordance with the multiple selected feature values or the combination of selected feature values.

Alternatively, the control may, in accordance with the selected feature value or the combination of selected feature values from the (maximum) number of stored test methods, first display selectably to the user on the display means (only) the test methods that are suitable for the selected feature or the combination of selected feature values. The user can then select one or more test methods from the test methods preselected by the control in this way and displayed on the display means.

In accordance with the test method selected either automatically by the control directly or by the user selecting in the way described, the testing of the test objects is later performed.

The test methods generally comprise at least test algorithms, in particular image evaluating methods, with the aid of which the evaluating device of the testing device performs an evaluation of images of the test object recorded in the course of testing the test objects by the testing device. For example, images of the test objects can be recorded with the testing device during the testing and evaluated with the evaluating device of the testing device with the aid of the test methods. The evaluating device in this case uses test methods which comprise suitable, software-based or electronic image evaluation methods.

According to a first test method, the recorded images could for example be compared with stored reference images to detect defects of the test objects. Moreover, the position of objects in the recorded images could be determined or checked by a second test method or an image evaluation method of the second test method. Such a test method could in fact comprise for example the checking of the correct position of the edges of a banderole on a top side of a cigarette pack.

In the aforementioned example, the setting up of the testing device, to be specific in this case the setting up of the evaluation device of the testing device, is ultimately indirectly dependent on the selection of the feature value or values by the user. This is so because the selection initially influences the type of test methods that are either directly selected by the control or displayed on the display means in the course of the described preselection. The test method(s) that is/are finally selected ultimately (by the user or by the control) in turn influences/influence the setting up of the evaluating device, in that it uses these test methods or test algorithms assigned to the test methods in the course of the testing operations on the test objects.

In a development of the invention, the control of the testing device selects in advance, and in accordance with the at least one test method selected automatically or by the user, parameters that are used by the testing device in the course of the later testing of the test objects from a number of parameters respectively stored for the testing device in a data memory and transmits them to the testing device. Such parameters may be for example setting parameters for the illuminating device and/or the light detector of the testing device. Alternatively or in addition, they may be parameters which the evaluating device needs or uses in the course of testing the test objects for an image evaluation of the images recorded from the test objects.

Alternatively or in addition, certain parameters for the illuminating device and/or the evaluating device and/or the light detector that are to be used during the testing of the test objects by the illuminating device or the evaluating device or the light detector may also be determined in advance in some other way. The determination is in this case performed in the course of a special automatic calibration of a specimen or reference test object.

For this purpose, a user arranges a reference test object, in particular at the later testing position of the test objects. To simulate the later test conditions, the control sets the illuminating device for example to stored starting parameters, so that an illuminating element of the illuminating device illuminates the test object. For example, the light intensity of the illuminating element may be set to a stored starting light intensity. The light detector, generally a camera, subsequently records at least a first image of the reference test object illuminated in this way. The recorded image is then evaluated or analyzed. If the recorded image does not correspond to predetermined criteria, for example is overexposed or underexposed, the control changes the set parameters of the illuminating device. That is to say that the control changes for example the light intensity of the illuminating element of the illuminating device. Subsequently, at least one further image of the illuminated test object is recorded. This further image is also tested with regard to the predetermined criteria. The control repeats the aforementioned steps until one of the respectively recorded images corresponds to the predetermined criteria. The parameters that are set on the illuminating device at the end of the calibrating operation, that is to say when one of the recorded images corresponds to the predetermined criteria, are then used as parameters for the later testing operation. Of course, parameters of other devices of the testing device, for example the sensitivity of the light detector or the camera, may also be determined in this way in the course of this calibrating operation.

As far as the predetermined criteria that the respective image has to satisfy in order that the control ends the calibrating process are concerned, they may be for example brightness limit values or brightness setpoint values, which the image and/or parts of the image and/or groups of pixels or image dots of the same must satisfy.

In a development of the invention, the control first displays to the user the test object on the display means. Then the user can select with the input device at least one region of the displayed test object in which the test object is to be tested by the testing device. The control visually highlights this selected region on the display means. The selection of this region has the consequence that only the selected region is tested with the testing device. For example, the user can delimit a specific test region of a banderole to be tested.

Subsequently, the control may for example set the light detector of the testing device and/or the illuminating device exactly on this region. Alternatively or in addition, it is conceivable that a or the evaluating device of the testing device that performs the evaluation of images recorded by the testing element exclusively evaluates the selected regions.

In addition or alternatively, it is conceivable that the user can use the input device to cut out a region of the test object in which it is not to be tested. The evaluating device and/or the light detector would then ignore this region.

With the present invention, the setting up of the testing device is made much easier in comparison with the necessary measures of the prior art. The control of the testing device preferably guides the user interactively for this purpose. In particular by displaying features characterizing the test object or by the possibility that a user can select the suitable feature values from a set of feature values shown in advance for the test object actually to be tested, the setting up of the testing device is significantly simplified.

The setting up of the testing device is simplified still further if suitable help displays, for instance help images and/or help texts, are displayed on the display means, comprising tips on the feature-value alternatives and/or the selectable regions. For example, it may be envisaged to display or show these when the user uses the input device to select a suitable help field displayed on the display means.

The object of the invention is also achieved by a method for the optical testing of objects to be tested—test objects—during the production and/or packaging of cigarettes, in particular of cigarette packs and/or blanks for cigarette packs and/or overprints and/or print substrates on or for cigarette packs, with the aid of a suitable testing device, in particular as claimed in one or more of the claims, characterized by the following features: a) feature values of features characterizing the test object, in particular in a visual respect, are stored by means of an input device, for instance a keyboard or a pointing device, in a data memory and/or feature values of such characterizing features are determined at least partly automatically, preferably fully automatically, by evaluation of at least one image of a reference test object and/or of a blank for such reference test object recorded by means of an electrooptical testing element, in particular a camera; b) the testing device is set up or preset for the subsequent testing operations, in particular an evaluating device and/or an illuminating device and/or a suitable light detector of the testing device, the stored and/or determined feature values influencing the setting up of the testing device; c) the test objects are tested with the set-up testing device, and a device for the optical testing of objects to be tested—test objects—during the production and/or packaging of cigarettes, in particular of cigarette packs and/or blanks for cigarette packs and/or overprints and/or print substrates on or for cigarette packs, in particular for carrying out the above method, with the following features: a) an input device with which feature values of features characterizing the test object, in particular in a visual respect, of the test object to be tested and/or of a blank for the test object can be stored in a data memory assigned to an evaluating device; and/or b) a control device with which such feature values can be determined automatically or partly automatically by evaluation of images of a reference test object and/or of a blank for a reference test object that are recorded by means of an electrooptical test element, wherein c) the control device can be used for setting up the testing device, in particular an evaluating device of the testing device, an illuminating device of the testing device and/or a suitable light detector of the testing device, the stored and/or determined feature values influencing the setting up of the testing device.

Accordingly, for the setting up of the testing device, feature values of features characterizing the test object, in particular in a visual respect, are stored by the user—generally before the beginning of production or testing—by means of the input device in a data memory, for instance on a computer hard disk or the like. Alternatively or possibly in addition, the feature values of such features are determined by the control at least partly automatically, preferably fully automatically, by evaluation of at least one image of a reference test object and/or of a blank and/or print substrate for such a reference test object recorded by means of the electrooptical testing element, in particular a camera. Subsequently, the testing device is automatically set up by the control, the feature values that are either stored by the user and/or recorded partly or fully automatically influencing this setting up. The test objects are later tested with the testing device set up in this way.

In the case of this embodiment of the invention, it is accordingly possible in principle to dispense with a selection of feature values from a set of feature-value alternatives displayed for a feature. This embodiment may however also be combined with the steps or part-steps of the embodiment of the invention described further above.

Thus, for example, it is conceivable that either the control selects the at least one suitable test method in accordance with the feature values which have been stored or determined for the features that characterize the test object in the way described further above from the number of stored test methods, or that the control displays to the user multiple suitable test methods for selection, from which the user then selects at least one suitable method.

As far as the feature values that are stored and/or determined are concerned, they are preferably design data of the test object, such as for instance pack dimensions or score dimensions, and/or of the blank for the test object. They may also be data, in particular dimensions and/or positional indications, for image objects arranged on the test object and/or on the blank or alphanumeric characters.

With the aid of suitable algorithms, the control preferably subsequently determines an image, particularly with a spatial effect—a 3D image—, of a reference test object that can be folded from the blank from the user-entered design data of the blank for the reference test object and/or the data for the image objects/alphanumeric characters, and possibly from further characteristic features or data.

In a development of the invention, the control or the evaluating device of the testing device uses the determined image of the reference test object that can be folded from the blank in the subsequent testing of the test objects as a reference image, which is respectively compared at least in certain regions with at least one image or part-image of the respective test object to be tested that is recorded by the testing device during the testing of the test objects.

Correction parameters, in particular correction parameters by which influences of the testing device on the depiction of the test object recorded during the testing operation are addressed, are preferably included in the determination the reference image. These may be in particular influences of the optical system of the electrooptical testing element of the testing device and/or influences of the electronics of the electrooptical testing element.

Alternatively or in addition, foreseeable systematic deviations of the actual test objects produced from an ideal test object may be included in the determination of the reference image. For example, a cigarette pack actually folded from a blank generally deviates from a "virtual" cigarette pack theoretically calculated from the design dimensions of a prescribed blank. Thus, for example, roundings occur at the folding lines in the course of the actual folding operations, and lead to a deviation of the actual cigarette pack from the theoretically calculated pack. Such systematic deviations may be included in the theoretical determination of the reference image of the reference test object.

In a development of the invention, image objects and/or alphanumeric characters arranged on the reference test object or on the blank for the reference test object are detected in the automatic or partly automatic determination of the feature values of the characteristic features.

In a development of the invention, one or more image objects and/or alphanumeric characters arranged on the blank for the reference test object is or are disregarded or ignored in the comparison of the test objects with the reference test object in the course of the subsequent testing of the test objects.

The regions or the image objects/alphanumeric characters that are to be ignored in the subsequent testing of the test objects are preferably manually selected by the user, by means of the input device, to be disregarded. However, a corresponding automatic or partly automatic selection of such regions or such image objects/alphanumeric characters is also conceivable.

BRIEF DESCRIPTION OF THE DRAWINGS

Further features of the present invention emerge from the accompanying dependent claims, the following description of preferred exemplary embodiments of the invention and the accompanying drawings, in which:

DETAILED DESCRIPTION OF PREFERRED EMBODIMENTS

Figure 1:
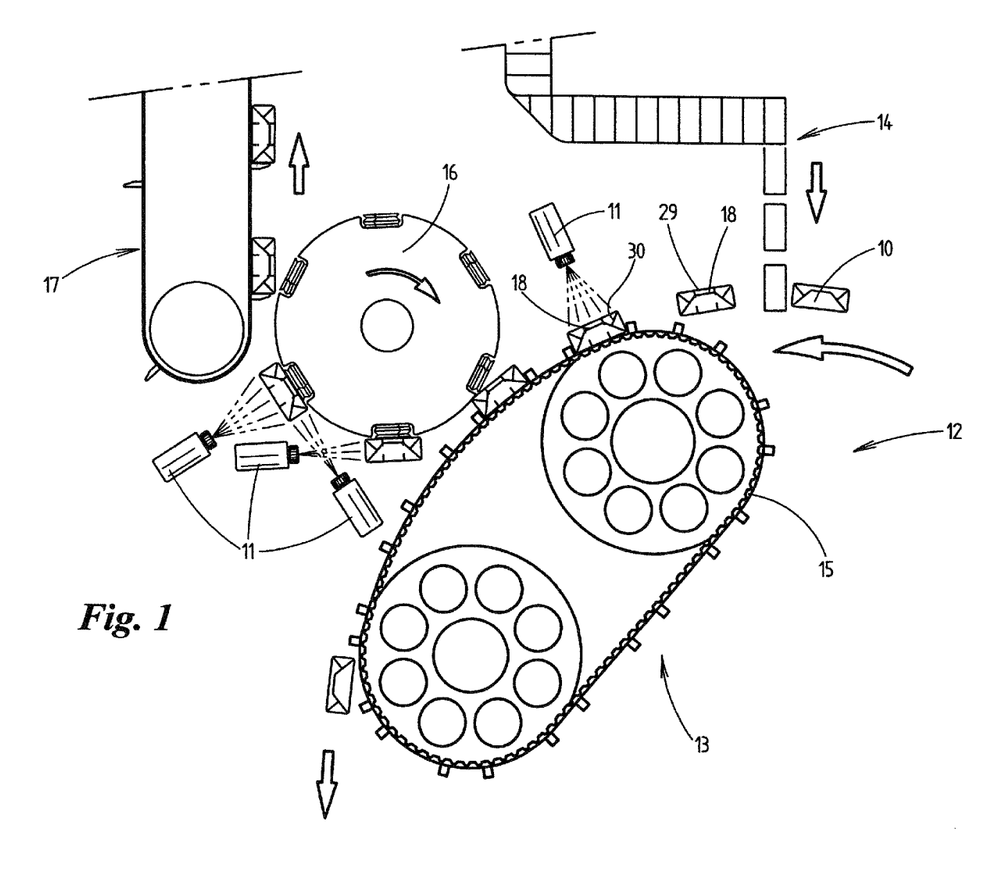
FIG. 1 shows a schematic representation of part of a packaging machine for soft-carton packs.
Figures 4, 5:
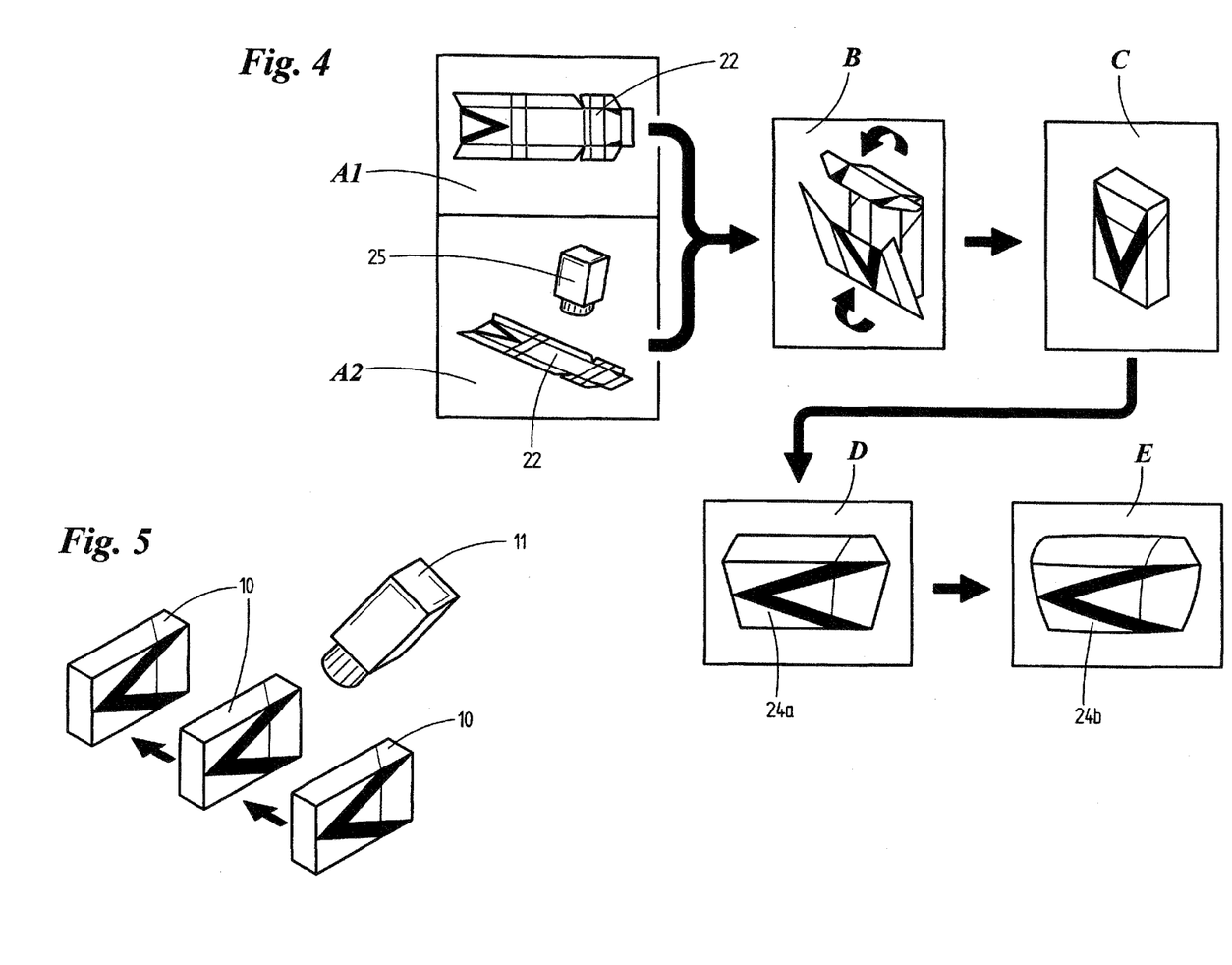
FIG. 4 shows a schematic representation of an alternative procedure for setting up the testing device.
FIG. 5 shows a schematic representation of the optical testing of a hinge-lid cigarette pack.

FIG. 1 shows by way of example parts of a device for producing cigarette packs 10, to be specific a packaging machine. The device can produce cigarette packs 10 of the soft-carton type or soft packs. However, according to the invention, the type of cigarette packs that can be produced is not important. For example, the invention can also be used in connection with devices for producing packs 10 of the hinge-lid type, but also in connection with carton packers, film packers or the like. The testing of hinge-lid packs is shown in FIG. 4.

The schematic representation shows a cutout of the packaging machine in which the packs 10 or details of the same are optically tested by means of a testing device. The testing device has inter alia electrooptical testing elements 11, in the present case CCD cameras.

The testing elements 11 in the present case record all sides of the cigarette packs 10, even if the recording of the top sides 29 and the bottom sides 30 of the packs is not explicitly shown. In the region of the packaging machine that is represented in FIG. 1, the individual packs 10 have already been largely completed and are being transported on a drying turret 12 for a lengthy period of time in the direction of rotation represented, in order that glued locations of the packs 10 can set and the exact format of the packs 10 is thereby stabilized. The packs 10 leave the drying turret 12 by way of a discharging device 13, which in the present case is formed as a belt conveyor.

Details of the structure and the operating principle of the drying turret 12 and the discharging device 13 can be taken from EP 0 605 838, to which reference is made for the purpose of complete disclosure and the content of which is made the subject of the present application to its full extent. Furthermore, this document also discloses the feeding of banderoles 14 and their attachment to the packs 10.

The packs 10 are taken off from the periphery of a conveying strand 15 of the discharging device 13 by a transfer device, in the present case a rotatably driven discharge wheel 16, and transferred directly to an upright cigarette conveyor 17. Details of the discharge wheel 16 are described in EP 0 770 551, of the cigarette conveyor 17 in EP 0 596 387. Reference is also made to these applications for the purpose of complete disclosure. The content of this application is made the subject of the present application.

As can partially be seen, for testing the packs 10, a pack side of the pack 10 is respectively assigned to a testing element 11. The images recorded by the respective testing element 11 of the testing device are analyzed in an evaluating device (not represented) of the testing device. The analysis generally serves primarily for the detection of defects of the pack respectively produced. Defective packs can consequently then be discharged from the production process.

The evaluating device may for example be part of the control or control device (likewise not represented) of the testing device, with which inter alia the individual testing elements 11 can be controlled. The evaluating device may of course also be a separate unit, for example a customary computer device with corresponding image-evaluation or analysis software for the evaluation of images of the packs 10 or of the respective pack sides that are recorded by the testing elements 11.

The testing device is adjusted to the kind of pack or pack type to be examined. Depending on the pack type or depending on the cigarette brand produced, the packs 10 differ. For instance, the packs 10 may have different banderoles 14, different overprints and so on. Different materials, colors, overprints, contrasts, etc. generally require different settings of the testing device.

An important particular aspect is that, when adjusting the testing device to the brand respectively produced or the pack type respectively produced, that is to say when setting up the testing device, the user is supported by the control of the testing device.

This is explained below by way of example on the basis of FIGS. 2 and 3 with regard to the testing of the pack top sides 29 and the bottom sides 30 of the packs 10. In actual fact, in the way described below, the testing device, in particular the evaluating device of the testing device, is set up automatically by the control on the basis of a selection, to be performed by a user, of feature values for specific features of the pack 10. Of course, other units of the testing device may also be automatically set in this way by the control, depending on selection decisions of the user.

If the testing device is to be adjusted to the testing of a pack 10 to be newly produced, features or feature values of cigarette packs that visually characterize the cigarette packs and are important for the setting up or setting of the testing device are first displayed to the user by the control on a display means or a screen. In this case, for each feature a set of feature-value alternatives is displayed on the display means and the user can select from this set the feature value that corresponds to the corresponding feature value of the pack 10 to be newly produced and to be tested with the testing device in the later testing.

Figure 2:
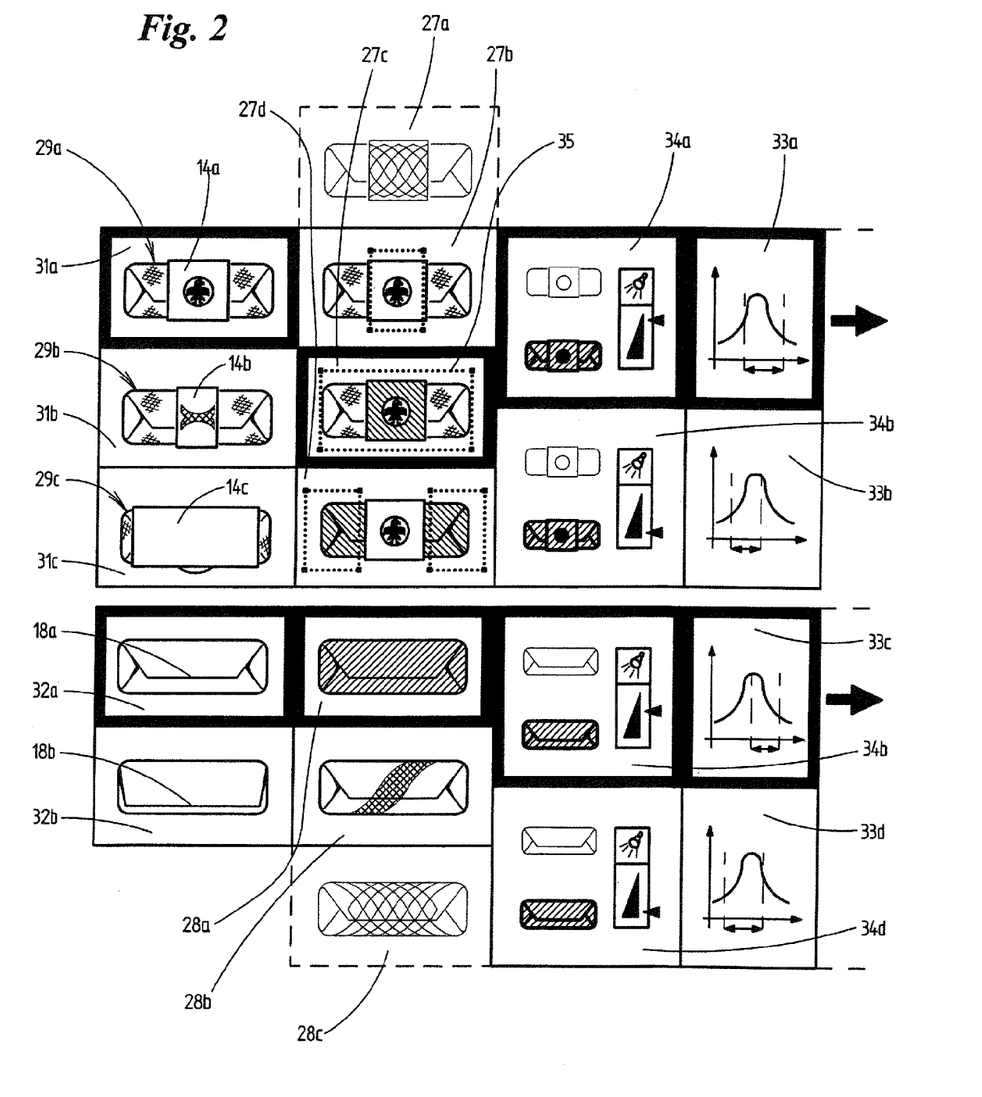
FIG. 2 shows a schematic partial representation of the sequence of setting up a testing device of the packaging machine.

For example, in FIG. 2 three top sides 29*a-c* of cigarette packs, on each of which different types of banderole 14*a*, 14*b*, 14*c* lie, are graphically represented. By means of an input device, for example a pointing device, such as for instance a mouse, the user can then select the combination 31*a-c* of top side 29*a-c* and banderole type 14*a*-14*c* that corresponds to the combination of top side 29 and banderole type 14 that, according to FIG. 1, the pack 10 to be newly produced has. The three different combinations 31*a-c* of top sides 29*a-c* with banderole types 14*a*-14*c* accordingly form feature-value alternatives of a "top side/banderole" feature.

In order to simplify the representation of the feature-value alternatives and the selection by the user, the display means may be part of a touchscreen, which serves at the same time as an input device.

Also shown in FIG. 2 are combinations 32*a-b* of two bottom sides 30*a-b* of cigarette packs, each bottom side 30*a-b* having a different bottom folding 18*a* and 18*b*, respectively. The user can select which of the two combinations 32*a-b* of bottom side 30*a-b* with bottom folding 18*a*, 18*b* corresponds to the bottom side 30, shown in FIG. 1, of the cigarette packs 10 to be newly produced. The two different combinations 32*a-b* of bottom sides 30*a-b* with bottom folding 18*a*, 18*b* accordingly form feature-value alternatives of a "bottom side/bottom folding" feature.

Apart from these examples, there may be many further characteristic features for which the control suggests feature-value alternatives to the user for selection.

It is also within the scope of the invention that none of the feature values 31*a-c*, 32*a-b* corresponds exactly to the corresponding feature value of the packs 10 to be newly produced. In such a case, the user may for example select the feature value that comes closest to that of the pack 10 to be produced.

The selection of the feature values 31*a-c*, 32*a-b* by the user for the features respectively characterizing the packs 10 influences the later setting up of the testing device by the control. Thus, depending on the selection of feature values made, the control first selects from a prescribed number of test methods the test method that can be used in the case of these feature values.

In the example of FIG. 2, the combination 31*a* of top side 29*a* and banderole 14*a* and the combination 32*a* of bottom side 30*a* and bottom folding 18*a* have been selected by the user. In a data memory, the individual feature values 31*a-c* are respectively assigned test methods 27*a-d*, the feature values 32*a-b* are respectively assigned test methods 28*a-c*.

On the basis of the combination 31*a* of top side 29*a* and banderole 14*a* selected by the user, the control selects from the test methods 27*a-d* that would be conceivable in principle for various combinations of top sides/banderoles and are stored in the data memory the test method 27*c* assigned to the selected combination 31*a*.

On the basis of the combination 32*a* of bottom side 30*a* and bottom folding 18*a* likewise selected by the user, the control also selects from the test methods 28*a-c* that would be conceivable in principle for various combinations of bottom sides/bottom foldings and are stored in the data memory the test method 28*a* assigned to the selected combination 32*a*.

Behind the test methods 27*a-d* and 28*a-c* there are inter alia various image evaluation methods or test algorithms with which the images recorded during the testing of the packs 10 can be evaluated by the evaluating device of the testing device.

The test method 27*c* may for example comprise a test algorithm with which the correct positioning and/or formation of the banderole 14 on the top side 29 of the cigarette pack 10 is tested with the aid of a suitable image evaluation method in the course of the later testing process. The test method 28*a* could on the other hand comprise a test algorithm that tests the correct positioning and/or formation of the folding 18 on the bottom side 30 with the aid of another suitable image evaluation method.

The selection of the test method 27*c* or the test method 28*a* by the control may also for example respectively necessitate a filtering algorithm assigned to the test method 27*c* or the test method 28*a* (for example Sobel filter, gray-morph filter). The respective filtering algorithm would be correspondingly used by the evaluating device in the electronic image detection or image evaluation of the images of the pack top sides 29 or the pack bottom sides 30 recorded in the course of the later testing of the cigarette packs 10.

To achieve optimum evaluation results, the test methods 27*c* and 28*a* are in this case adapted to the test objects respectively to be tested, in the present case the test objects comprising top side 29 and banderole 14 and comprising bottom side 30 and folding 18.

The banderole 14 to be tested of the cigarette pack 10 is for example a type of banderole that has a pattern on a dark blank or background. The top side 29 to be tested of the pack 10 consists of a dark silver foil with highly reflective properties.

A different constellation, and consequently a different selection from the feature values 31*a-d* by the user, in which for example a light banderole were arranged on a dark, non-reflective top side, could for example require use of the test method 27*d* with a different assigned filter, instead of use of the test method 27*c*, to allow optimum evaluation results to be achieved.

It is also provided that, with the aid of the input device, the user can cut out specifically determined regions of the pack 10 that can only be recorded with difficulty in the course of the automatic evaluation and are not to be tested by the testing device. In other words, in the present case for example it would not be the entire pack side 29, 30 of the pack 10 that were tested in each case, but only a cutout of the same.

Figure 3:
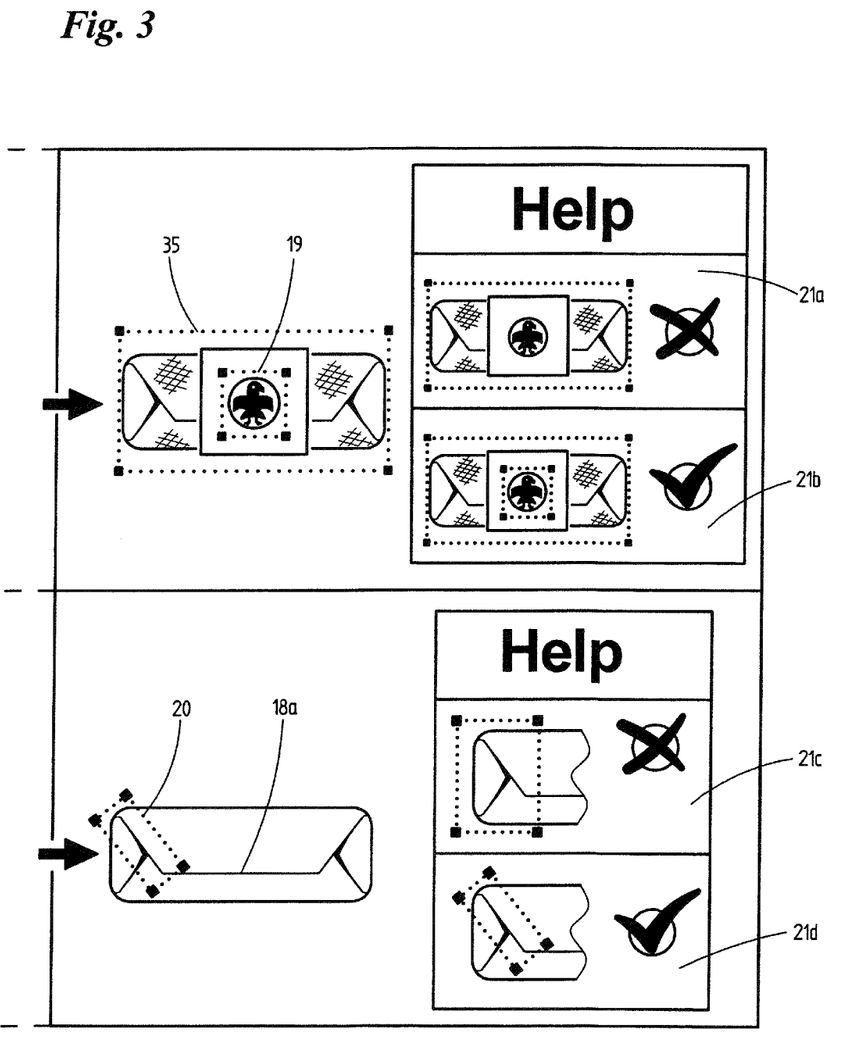
FIG. 3 shows a further schematic partial representation of the sequence of setting up the testing device of the packaging machine.

In the example of FIGS. 2 and 3, the user has cut out the pattern of the banderole 14a. The cut-out region is visually highlighted on the display means, in the present case by a dotted line 19. The cut-out region is ignored by the evaluating device during the image evaluation in the course of the later testing of the cigarette packs 10.

In a similar way, the user can specify more precisely certain regions in which the test objects are to be tested. For example in the case of the selected bottom folding 18a of the combination 32a, the user may select the region of the folding 18a that is to be specifically tested. The selected region is likewise visually highlighted on the display means, in this case by a dotted line 20. The evaluating device would only consider or evaluate this region in the image evaluation in the course of the later testing of the cigarette packs 10.

Moreover, it may be provided that help displays are shown to the user, comprising tips on feature-value alternatives and/or selectable regions. In the present example, either automatically or on request by the user, for example by the user using a pointing device to click a help field, two helping tips 21a and 21b are displayed for the region of the banderole 14a that can be cut out. In this case, tip 21a serves the purpose of pointing out to the user that it would be inadvisable to forego cutting out of the pattern of the banderole 14a. The tip 21b indicates that the pattern should be cut out correctly.

In a similar way, help displays 21c, 21d are displayed to the user for the selectable regions of the bottom folding 18a.

According to a further important aspect of the invention, which is illustrated by the boxes 34a-d in FIG. 2, parameters of illuminating devices 26, which illuminate the packs to be tested during the later testing operation in order to achieve greatest possible contrast between different image components in the case of the images recorded by the testing elements or cameras 11, are automatically determined in the course of a separate calibrating operation of a specimen or trial pack.

In this respect, the user arranges reference or specimen packs respectively at the later testing position of the cigarette packs 10, that is to say at the testing positions from FIG. 1. To simulate the later test conditions, the control of the testing device then sets the illuminating devices 26 (not shown in FIG. 1) to stored starting parameters, so that the illuminating elements of the illuminating devices 26 illuminate the corresponding pack sides of the cigarette packs, for example the top side 29a with banderole 14a and the bottom side 32a with bottom folding 28a that are shown in FIG. 2.

In this case, the light intensity of the respective illuminating element of the respective illuminating device 26 may first be set respectively to a stored starting light intensity. The respective camera 11 subsequently records at least one image of the respective pack side illuminated in this way. The recorded image is then evaluated or analyzed by the evaluating device.

If the recorded image does not correspond to predetermined criteria, the control changes the set parameters of the respective illuminating device 26, to be specific in the present case the light intensity, until the aforementioned criteria are satisfied.

In the example of FIG. 2, it is symbolized by the box 34a and the assigned box 33a that, to achieve optimum results in the calibration of the top side 29a with the banderole 14a in the recorded image, a large proportion of overexposed image dots in the overall number of image dots of the recorded image is accepted in the course of the image evaluation. Furthermore, to achieve an optimum result in this constellation, the entire top side 29a with banderole 14a is measured in the course of the calibrating operation, cf. dotted line 35.

The background of the calibration of the entire region 35 is that, with the selected combination 31a of silver-foil top side 29a and dark banderole 14a, the disturbing reflections of the silver-foil top side are great. The background of the acceptance of a high proportion of overexposed image dots is that the light intensity must be as high as possible in order in the case of this constellation of a low intrinsic contrast between the dark banderole 14a and the dark top side 29a to detect for example in the image evaluation edge transitions between the almost similarly dark banderole 14a and the top side 29a.

The control then changes the light intensity of the respective illuminating element of the respective illuminating device 26 in the course of the calibration until a certain proportion of image dots of the recorded image has a predetermined brightness value.

In the case of another constellation, symbolized by box 34b, in which there is a high intrinsic contrast between the banderole and the top side, for example in the case of a light banderole on a dark top side, the illuminating intensity would be changed in the course of the calibrating operation until a correspondingly low proportion of image dots in the recorded image had a certain brightness value that is lower in comparison with the constellation 34a. In other words, in the constellation according to box 34a, fewer overexposed image dots in the recorded image are accepted than would be the case in the constellation according to box 34b. Moreover, it would be conceivable in the constellation according to box 34b to dispense with the calibration of the entire top side and to calibrate essentially only the banderole.

The actual light intensity, and possibly other parameters of the illuminating device 26 that are set at the end of the calibrating operation, that is to say when the predetermined criteria that the respectively recorded image must satisfy are met, are then used as setting parameters of the illuminating device 26 for the later testing operation on the top sides of the packs 10. Of course, parameters of other devices of the testing device, for example the sensitivity of the respective camera 11, could also be determined in this way in the course of this calibrating operation.

In a similar way, the illumination parameters for the illumination of the bottom side 30a with bottom folding 18a are determined in the course of a further calibrating operation, to be precise ultimately depending on the intrinsic contrasts between the bottom side 30a and the bottom folding 18a (boxes 34c, d).

Figure 6:
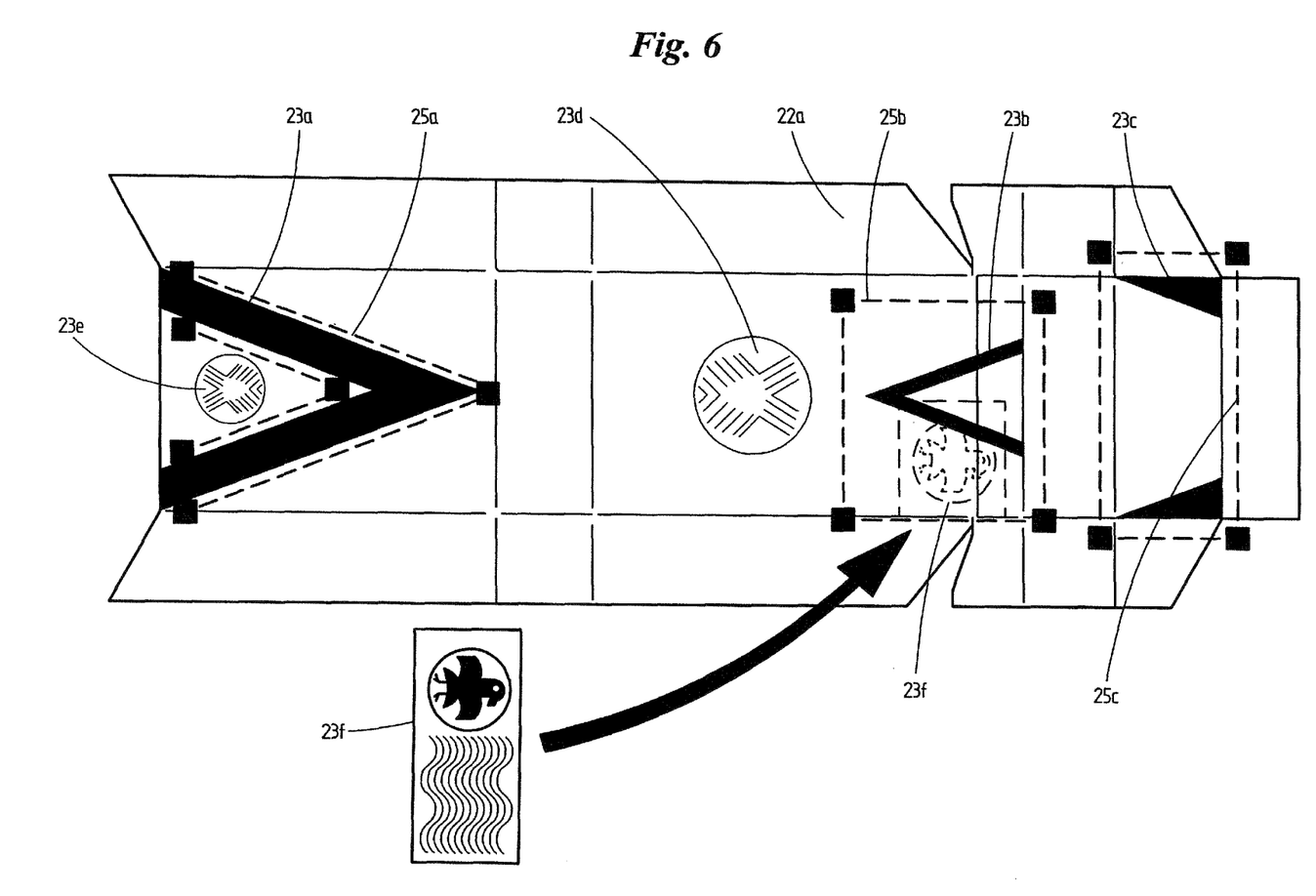
FIG. 6 shows a blank for a reference cigarette pack that is used in the course of the alternative procedure according to FIG. 4.

FIGS. 4-6 show a further embodiment of the invention. It concerns the production and testing of packs 10 of the hinge-lid type. These are folded or produced from blanks.

Unlike in the case of the embodiment of FIGS. 1, 2 described above, lists of feature values of features characterizing the pack are not displayed to the user when setting up the testing device for the pack 10 to be newly produced. Rather, the sequence of events is as follows:

According to a first alternative of the further embodiment, a user can store feature values of the pack 10 by means of the input device in a data memory assigned to the control of the testing device (step A1 in FIG. 3). In the present case, the data memory is for example a hard disk. All other known data memories can of course also be used. In the data memory there may be database software, to which the feature values are written.

Design data of a specimen or reference blank 22 for the packs 10 may be stored for example as feature values. The design data may describe dimensions of the blank 22, the position and length of the individual folding lines of the blank 22, the size and/or the forms of the individual folding flaps and the like. The user can derive these design data from the reference or specimen blank 22.

Apart from the design data, the user may also store further data, in particular data on image objects 23a, 23b, 23c, 23d, 23e arranged on the blank 22 or the later pack 10. These data on the image objects 23a-e comprise in particular the type, form, color, position and/or size of the image objects and the like.

It is conceivable in this respect that the user first uses the input device to select from a selection of different image objects already stored in the data memory the image objects 23a-e that coincide with the specimen blank 22. Alternatively, specifically only the image objects 23a-e may be stored as files or stored directly for the setting-up operation of the testing device for the pack 10 to be newly produced, so that the selection of the correct image objects 23a-e from a suggested set of image objects is dropped.

The image objects 23a-e may in this case be stored in the data memory, in that for example the specimen blank is scanned in, or individual regions of the same that have the individual image objects are scanned in. Then individual image files of the image objects can be respectively produced from the scanned-in image data.

The user can then position the stored image objects 23a-e on a (virtual) depiction 22a (FIG. 6) of the blank 22 that is calculated from the previously stored design data for the pack 10 or the specimen blank 22 and displayed on the screen in the same way as they are arranged on the (actual) specimen blank 22. Alternatively, positioning of the image objects 23a-e on the depiction 22a of the specimen blank 22 on the basis of position indications that the user stores with the input device is of course also possible.

Furthermore, a depiction 23f of a banderole to be placed on the pack 10 may also be stored separately as an image file and positioned on the virtual blank 22a.

As a result, all of the items of information or data, including the image objects, concerning the actual specimen blank 22 or the pack 10 to be produced that are necessary to be able to calculate the image 22a of the pack 10 that can be folded from the blank 22, in particular by means of suitable software, are stored in the data memory.

According to a second alternative of the further embodiment, to be specific as an alternative to the manual storing of the design data described above and the data of further characterizing features of the blank 22 by a user, it is envisaged to allow these data to be recorded automatically or at least partly automatically by the control.

For this, first an actual reference blank 22 of the packs 10 to be produced is recorded by a suitable recording element 25, generally a camera. In other words, the depiction 22a of the actual reference or specimen blank 22 is automatically produced (step A2 in FIG. 3) and automatically stored in the data memory of the control device.

In an almost fully automatic variant, all of the design data and all of the further data (image object data etc.) that in the first variant were entered manually by the user are then determined by suitable analysis from the depiction 22a recorded by the camera, or are extracted from the depiction 22a with the aid of an evaluating device (for example a computer device), which is generally part of the control. The software of the evaluating device that is necessary for such an analysis of the depiction of the specimen blank 22 can be readily provided by a person skilled in the prior art.

It is conceivable in this respect that the user selects individual regions 25a, 25c of the depiction 22a of the blank 22 in order to simplify the detection of the individual image objects arranged on the depiction 22a in the course of the analysis described above of the depiction 22a, in this case the image objects 23a, 23b, 23c.

It is also conceivable to record, likewise with the recording element 25, separate print substrates that are to be arranged on the cigarette pack 10, such as for instance the banderole 23f, to store a depiction of the same, possibly derive necessary data and possibly arrange the depiction of the blank at a certain position of the depiction 22a of the blank 22, likewise automatically.

The arrangement of the depiction 23f on the virtual depiction 22a of the blank 22 may alternatively also be carried out manually by a user.

As soon as all of the design data, graphics, possibly alphanumeric characters, etc. of the blank 22 have been stored (alternative 1), or all of the data have been automatically derived from the depiction 22a of the recorded blank 22, recorded by means of the camera 25 (alternative 2), the evaluating device calculates an image 24a of the virtual cigarette pack 10 obtained from these data (steps B, C, D in FIG. 3). In this case, a three-dimensional (virtual) depiction of the cigarette pack 10 is preferably produced. In other words, an image 24a of the pack 10 that can be folded from the blank 22 is produced.

Subsequently, in a way described more specifically below, a reference image 24b is produced from the three-dimensional image 24a (step E). This reference image 24b serves as a comparative image during the testing of the cigarette packs 10 actually produced in the later production process. The reference image 24b, or possibly parts of the same, are thereby compared with images of the cigarette packs 10 actually produced that are recorded by the testing device or the testing elements 11. Deviations of the recorded images from the reference image 24b may then be recorded and defects of the cigarette packs 10 produced can then be discovered in a way known per se.

Correction parameters, which for example address influences of the testing device on the image recorded by it of the packs 10 actually produced, are then included as one of the factors in the determination of the reference image 24b. For instance, the testing elements 11 of the testing device generally have optical aberrations or produce such aberrations. Such aberrations can be calculated into the reference image 24b, so that they are automatically ignored in a comparison of the reference image 24b with the packs 10 actually produced.

The electronic components of the testing elements 11 may also produce aberrations that lead to images that are distorted in comparison with reality.

Apart from these correction parameters, which address influences of the testing device on the depiction recorded by it of the pack respectively to be tested, alternatively or in addition, foreseeable systematic deviations of the test objects 10 actually produced from the (virtual) depiction 24a of the cigarette pack 10 calculated in the way described above may be included.

For example, the folding of the blank 22 along the folding lines in the actual production generally deviates from a theoretically calculated folding. Thus, for example, the actual foldings have roundings, which are included in the calculation in the determination of the reference image 24b.

Both in the case of the manual input described above of the data for the specimen blank 22 and in the case of the described automatic recording of the specimen blank 22, it is moreover possible to disregard individual, particularly complicated image objects 23e, 23d during the subsequent testing of the packs 10 produced. For this purpose, the image objects 23e, 23d may be automatically detected as to be ignored in further testing. However, it is also conceivable that the user manually selects the image objects 23e, 23d on the screen and these image objects 23d, 23e are disregarded on the basis of this manual selection.

| List of designations | |
|---|---|
| 10 | Pack |
| 11 | CCD camera |
| 12 | Drying turret |
| 13 | Discharging device |
| 14 | Banderole |
| 14a | Banderole type |
| 14b | Banderole type |
| 14c | Banderole type |
| 15 | Conveying strand |
| 16 | Discharge wheel |
| 17 | Cigarette conveyor |
| 18 | Bottom folding |
| 18a | Bottom folding |
| 18b | Bottom folding |
| 19 | Dotted line |
| 20 | Dotted line |
| 21a | Alternative |
| 21b | Alternative |
| 21c | Help display |
| 21d | Help display |
| 22 | Specimen blank |
| 22a | Depiction of specimen blank |
| 23a | Image object |
| 23b | Image object |
| 23c | Image object |
| 23d | Image object |
| 23e | Image object |
| 23f | Depiction of banderole |
| 24a | 3D image |
| 24b | Reference image |
| 25 | Recording element |
| 25a-c | Image regions |
| 26 | Illuminating device |
| 27a-d | Test methods pack top side |
| 28a-c | Test methods pack bottom |
| 29 | Top side |
| 29a-c | Top side |
| 30 | Bottom side |
| 30a-b | Bottom side |
| 31a-c | Combination of top side/banderole |
| 32a-b | Combination of bottom side/folding |
| 33a-d | Box |
| 34a-d | Box |
| 35 | Dotted line |

What is claimed is:

1. A method for setting up or presetting a testing device for the optical testing of test objects during the production and/or packaging of cigarettes, the method comprising:
    a) displaying on a display means of the testing device a set of feature values for at least one visual feature characterizing the test object, the at least one visual feature being selected from the group consisting of physical, surface, and optical features of the test objects, and the set of feature values previously being stored in a data memory;
    b) selecting at least one of the displayed feature values by means of an input device of the testing device;
    c) in accordance with the selected at least one of the displayed feature values, using a computer to automatically select at least one test method that is suitable for the test object to be tested from a number of test methods that are stored in the data memory and by which the test objects are to tested with the testing device;
    d) using the computer to automatically set up or preset at least one testing element of the testing device, the testing element being selected from the group consisting of an evaluating device, an illuminating device, and a suitable light detector, for subsequent testing operations on the test objects, wherein the selection of the at least one of the displayed feature values influences the setting up or presetting of the testing device; and
    e) testing the test objects with the set-up or preset testing device, wherein the test objects are at least one of a cigarette pack and blank for a cigarette pack.

2. The method as claimed in claim 1, further comprising selectably displaying from this number of test methods multiple test methods that are suitable for testing the test object to be tested on the display means, whereby a user selects at least one of the test methods displayed.

3. The method as claimed in claim 2, further comprising performing the testing of the test objects in accordance with the at least one of the test methods selected automatically or by the user.

4. The method as claimed in claim 2, wherein the test methods comprise test algorithms and, with the aid of the test methods comprising the test algorithms, further comprising using the testing element for taking, recording, and evaluating images of the test objects in the course of the testing of the test objects.

5. The method as claimed in claim 2, further comprising selecting parameters that are used by the testing device in the course of the testing of the test objects in advance in accordance with the at least one test method selected automatically using the computer or by the user from a number of parameters respectively stored for the testing device in the data memory, and transferring the selected parameters to the testing device.

6. The method as claimed in claim 2, further comprising:
    In accordance with the at least one test method selected automatically using the computer, determining in advance parameters for the at least one testing element that are used by the testing element during the testing of the test objects;
    illuminating a reference test object, arranged at a later testing position of the test Objects with light of the illuminating device at a set light intensity;
    recording at least one image of the illuminated reference test object by the light detector;
    evaluating the recorded image of the illuminated reference test object by comparing the recorded image of the illuminated reference with predetermined criteria stored in the data memory; and
    if the recorded image of the illuminated reference test object does not correspond to the predetermined criteria, repeating the aforementioned steps with changed settings of the light intensity of an illuminating element of the illuminating device until the recorded image of the illuminated reference test object corresponds to the predetermined criteria.

7. The method as claimed in claim 1, further comprising displaying on the display means the feature values alphanumerically and/or as image objects.

8. The method as claimed in claim 1, further comprising:
    graphically displaying the test object on the display means;
    using the input means to select at least one of a region of the test object in which the test object is to be tested and a region in which the test object is not to be tested;
    using the input means to visually highlight the selected region on the display means; and testing only the selected region or only the non-selected region is tested with the testing device.

9. The method as claimed in claim 1, wherein the test objects are at least one of the following two groups of test object:
- pack top sides of a cigarette pack with a banderole arranged on them, wherein a set of various combinations of top sides with banderoles arranged on them is displayed selectably as a set of feature values; and
- pack bottom sides with bottom foldings of a cigarette pack, wherein a set of various combinations of bottom sides with bottom folding being displayed selectably as a set of feature values.

10. The method as claimed in claim 8, further comprising, after selecting the at least one of the displayed feature values with the input device, displaying help displays on the display means, the help displays comprising at least one of help images and help texts comprising at least one of tips on the feature values and the selected region.

11. a method for setting up or presetting a testing device for the optical testing of a test object during the production and/or packaging of cigarettes, the method comprising:
a) at least one of (i) storing feature values of visual features characterizing the test object by means of an input device in a data memory, and (ii) determining the feature values at least partly automatically using a computer by evaluation of at least one image of a reference test object recorded by means of an electrooptical testing element, the visual features being selected from the group consisting of physical, surface, and optical features of the test object;
b) selecting at least one of the feature values by means of the input device and using the compute to automatically select at least one test method that is suitable for the test object to be tested from the a number of test methods that are stored in the data memory and by which the test objects are to be tested with the testing device;
c) setting up or presetting at least one testing element of the testing device, the testing element being selected from the group consisting of an evaluating device, an illuminating device, and a suitable light detector, for subsequent testing operations on the test object, wherein the feature values influence the setting up of the testing device; and
d) testing the test objects with the set-up or preset testing device, wherein the test objects are at least one of a cigarette pack and blank for cigarette pack.

12. The method as claimed in claim 11, wherein the feature values are selected from the group consisting of design dimension data of the cigarette pack, design dimension data of the blank, dimension and/or position data concerning image objects arranged on the test object, and dimension and/or position data concerning alphanumeric characters arranged on the test object, and combinations thereof.

13. The method as claimed in claim 12, further comprising, with the aid of suitable algorithms and the computer, determining an image having a spatial effect of a reference test object that can be folded from the blank from at least the design data of the blank for the reference test object.

14. The method as claimed in claim 13, further comprising using the determined image of the reference test object that can be folded from the blank in the subsequent testing of the test object as a reference image, and using the computer to compare at least certain regions of the test object with the reference image.

15. the method as claimed in claim 14, further comprising at least one of:
including correction parameters in the determination of the reference image, the correction parameters addressing influences of the testing device on a depiction of the test object recorded during the testing operation, the influences being selected from the group consisting of influences of the optical system of the electrooptical testing element of the testing device and influences of the electronics of the electrooptical testing element; and
including foreseeable systematic deviations of an actual test objects produced or to be produced from an ideal determined or calculated test object in the determination of the reference image.

16. The method as claimed in claim 12, further comprising
Using the testing element to detect image objects and/or alphanumeric characters arranged on the reference test object or on the blank for the reference test object in the at least partly automatic determination of the feature values characterizing the test object.

17. The method as claimed in claim 14, further comprising disregarding or ignoring at least one region of the blank for the reference test object, the at least one region being image objects and/or alphanumeric characters arranged on the blank for the reference test object, in the comparison of the test objects with the reference test object in the course of the subsequent testing of the test objects.

18. The method as claimed in claim 17, further comprising manually selecting at least one of the regions by means of the input device, to be disregarded in the subsequent testing of the test objects .

19. A testing device for the optical testing of test objects during the production and/or packaging of cigarettes, comprising:
a) a display means on which, for at least one visual feature characterizing the test object , a set of feature values for the corresponding visual feature that are stored in a data memory is displayed, the visual feature being selected from the group consisting of physical, surface, and optical features of the test objects;
b) an input device with which the at least one visual feature of the displayed set of feature values is selected; and
c) a control device with which at least one testing element of the testing device, the testing element being selected from the group consisting of an evaluating device, an illuminating device, and a suitable light detector, is automatically set up, wherein the selection of the at least one visual feature influences the setting up of the testing device,
wherein the testing device is set up or preset for the optical testing of the test objects using a method comprising:
i) displaying on the display means the set of feature values;
ii) selecting at least one of the displayed feature values by means of the input device of the test device and using a computer to automatically select at least one test method is suitable for the test object to be tested object to be tested from a number of test methods that are stored in a data memory and by which the test objects are to be tested with the testing device;
iii) automatically setting up or presetting the at least one testing element for subsequent testing operations on the test objects; and
iv) testing the test objects with the set-up or preset testing device, wherein the test objects are at least one of a cigarette pack and a blank for a cigarette pack.

20. A testing device for the optical testing of test objects during the production and/or packaging of cigarettes, comprising:
a) an input device with which feature values of visual features characterizing the test object to be tested and/or of a blank for the test object is stored in a data memory cooperating with an evaluating device, the visual features being selected from the group consisting of physical, surface, and optical features of the test object; and
b) a control device with which the feature values are determined automatically or partly automatically by a computer by evaluation of images of a reference test object and/or of a blank for the reference test object that are recorded by means of an electrooptical test element, wherein the control device is used for setting up at least one testing element of the testing device, the testing element being selected from the group consisting of an evaluating device, an illuminating device, and a suitable light detector, wherein the feature values influence the setting up of the testing device, wherein the testing device is set up or preset for the optical testing of the test objects using a method comprising:
i) at least one of (i) storing the feature values, the feature values being visual features characterizing the test object, by means of the input device in the data memory, and (ii) determining the feature values at least partly automatically by the evaluation of the images of the reference test object recorded by means of the electrooptical testing element;
ii) selecting at least one of the feature values by means of the input device and using the computer to automatically select at least one test method that is suitable for the test object to be tested from a number of test methods that are stored in the data memory and by which the test objects are to be tested with the testing device;
iii) setting up or presetting the at least one testing element for subsequent testing operations on the test object; and
iv) testing the test objects with the set-up or preset testing device, wherein the test objects are at least one of a cigarette pack and a blank for a cigarette pack.

* * * * *